(12) United States Patent
Kharkar

(10) Patent No.: US 11,925,747 B2
(45) Date of Patent: Mar. 12, 2024

(54) DRESSING INTERFACE WITH MICRO-NEEDLES FOR NEGATIVE-PRESSURE TREATMENT

(71) Applicant: KCI Licensing, Inc., San Antonio, TX (US)

(72) Inventor: Prathamesh Madhav Kharkar, San Antonio, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 55 days.

(21) Appl. No.: 17/633,446

(22) PCT Filed: Aug. 25, 2020

(86) PCT No.: PCT/IB2020/057944
§ 371 (c)(1),
(2) Date: Feb. 7, 2022

(87) PCT Pub. No.: WO2021/038447
PCT Pub. Date: Mar. 4, 2021

(65) Prior Publication Data
US 2022/0287884 A1    Sep. 15, 2022

Related U.S. Application Data

(60) Provisional application No. 62/894,430, filed on Aug. 30, 2019.

(51) Int. Cl.
*A61F 13/00* (2006.01)
*A61F 13/02* (2006.01)
*A61M 1/00* (2006.01)

(52) U.S. Cl.
CPC ....... *A61M 1/915* (2021.05); *A61F 13/00068* (2013.01); *A61F 13/0216* (2013.01); *A61M 1/916* (2021.05); *A61M 2205/3344* (2013.01)

(58) Field of Classification Search
CPC ............ A61F 13/00068; A61F 13/0203; A61F 13/0216; A61F 2013/00417; A61M 1/85;
(Continued)

(56) References Cited

U.S. PATENT DOCUMENTS 1,355,846 A    10/1920  Rannells
2,338,339 A *  1/1944  La Mere ............... A61H 9/005
                                              15/387
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Andrew J Mensh
*Assistant Examiner* — Jihad Dakkak

(57) ABSTRACT

A dressing interface includes a base that has an aperture and a plurality of microneedles that are attached to the base and disposed over the aperture. The interface also includes a port that is configured to receive a fluid conductor and a conduit that couples the port and the aperture. Each of the microneedles contains a passageway that is fluidly coupled to the aperture. The interface may be used with a drape that is placed over a tissue site. The interface may provide communication between the tissue site and a reduced-pressure source through the microneedles piercing the drape rather than by cutting a hole in the drape.

20 Claims, 8 Drawing Sheets

(58) Field of Classification Search
CPC ........ A61M 1/90; A61M 1/912; A61M 1/913; A61M 1/915; A61M 1/916; A61M 1/92; A61M 1/94; A61M 2205/3344; A61M 37/00; A61M 37/0015; A61M 5/14; A61M 5/14248

See application file for complete search history.

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077584 A1* | 6/2002 | Lin ............... A61B 5/150984 604/21 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0219512 A1* | 9/2007 | Heaton ............... A61M 1/912 604/304 |
| 2010/0063464 A1* | 3/2010 | Meyer ............... A61M 27/00 604/319 |
| 2010/0228206 A1* | 9/2010 | Larsson ............... A61M 1/85 604/319 |
| 2010/0305524 A1* | 12/2010 | Vess ............... A61M 1/85 604/313 |
| 2014/0163491 A1 | 6/2014 | Schuessler et al. |
| 2014/0309619 A1 | 10/2014 | Agarwal et al. |
| 2015/0080788 A1 | 3/2015 | Blott et al. |
| 2017/0014606 A1* | 1/2017 | Locke ............... A61M 1/96 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |

(56) References Cited

FOREIGN PATENT DOCUMENTS

| | | | |
|---|---|---|---|
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2015116823 A1 | 8/2015 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. @ Therapy Clinical Guidelines: A Reference Source for Clinicians; Jul. 2007.
International Search Report and Written Opinion for Corresponding Application No. PCT/IB2020/057944 dated Nov. 27, 2020.

* cited by examiner

001# DRESSING INTERFACE WITH MICRO-NEEDLES FOR NEGATIVE-PRESSURE TREATMENT

CROSS-REFERENCE TO RELATED APPLICATIONS

This application claims the benefit of priority to U.S. Provisional Application No. 62/894,430, filed on Aug. 30, 2019, which is incorporated herein by reference in its entirety.

TECHNICAL FIELD

The invention set forth in the appended claims relates generally to tissue treatment systems and more particularly, but without limitation, to apparatuses, systems, and methods fluidly coupling a negative-pressure source to a dressing.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for treating a tissue site in a negative-pressure therapy environment are set forth in the appended claims. Illustrative embodiments are also provided to enable a person skilled in the art to make and use the claimed subject matter.

For example, in some embodiments, a dressing interface may include microneedles attached to the base of the interface. These microneedles allow the interface to penetrate the surface of a drape, fluidly coupling the interface to a dressing without cutting a hole in the drape or penetrating tissue. The microneedles may have a height that is between about 100 micrometers and 4000 micrometers so that the microneedles can penetrate the drape layer and a foam layer that may optionally be included in the dressing. The width of the microneedles may be between 200 micrometers and 2000 micrometers so that there is room for a hollow channel to run through each microneedle. The hollow channel may be between 20 micrometers to 1800 micrometers in width and could be tapered anywhere from 0 to 45 degrees. The microneedles may be similarly tapered so as to prevent the channels of the microneedles from being blocked by the drape when they first pierce the drape.

In some examples, the microneedles can be fabricated using a biocompatible material such as stainless steel, titanium, aluminum, polycarbonate, polyethylene terephthalate, polyetherketone, polyimide, or polyphenylsulfone. The microneedles may contain a microneedle substrate that is fabricated from the same biocompatible material as the microneedles themselves. In other examples, the microneedles may be coated with active agents such as anti-bacterial agents and biopolymers such as collagen and hyaluronic acid that assist in the process of wound healing.

More generally, some embodiments of a reduced pressure interface may include a port that is configured to receive a fluid conductor. The interface may also include a base that has an aperture and a plurality of microneedles disposed over the aperture. A conduit can fluidly couple the port and the aperture. In some examples, the conduit may comprise a bend between the port and the aperture. Further, each of the microneedles may contain a passageway that is fluidly coupled to the aperture. In some embodiments the microneedles may be arranged in an array over the aperture. The arrangement of the microneedles in an array can provide redundancy, preventing blockage because even if some channels are blocked, there will be others that can allow for effective and efficient fluid flow. In other embodiments the interface may include a microneedle substrate that is coupled to each of the microneedles as well as the base of the interface. This substrate may be adhered to the base of the interface by a pressure sensitive adhesive.

The interface may further include channels on the entry surface that are adapted to direct liquid into the port. In some embodiments, the port may comprise a primary lumen and one or more ancillary lumens. The channels may help guide liquid to a primary lumen, away from ancillary lumens, or both.

In other examples, the dressing interface may be used with a system for treating a tissue site with negative pressure. The system may include a manifold that is applied to the tissue site and a cover that is placed over the manifold. The dressing interface may be applied to the cover so that the microneedles pierce the cover.

Further, other embodiments may include a method for treating a tissue site with negative pressure. For example, a manifold may be applied to a tissue site and a cover may be sealed over the manifold and around a tissue site. A dressing interface with microneedles may be disposed on the cover. Pressure can be applied to the interface to pierce the cover with the plurality of microneedles. The pressure needed to penetrate the cover may be as little as approximately 2N. A fluid conductor can be fluidly coupled to a port on the interface and a negative-pressure source can be fluidly coupled to the fluid conductor. A therapeutic level of negative pressure from the negative-pressure source can be applied to the manifold through the fluid conductor and the interface. Additionally, or alternatively, a topical solution may be delivered to the manifold through the interface.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
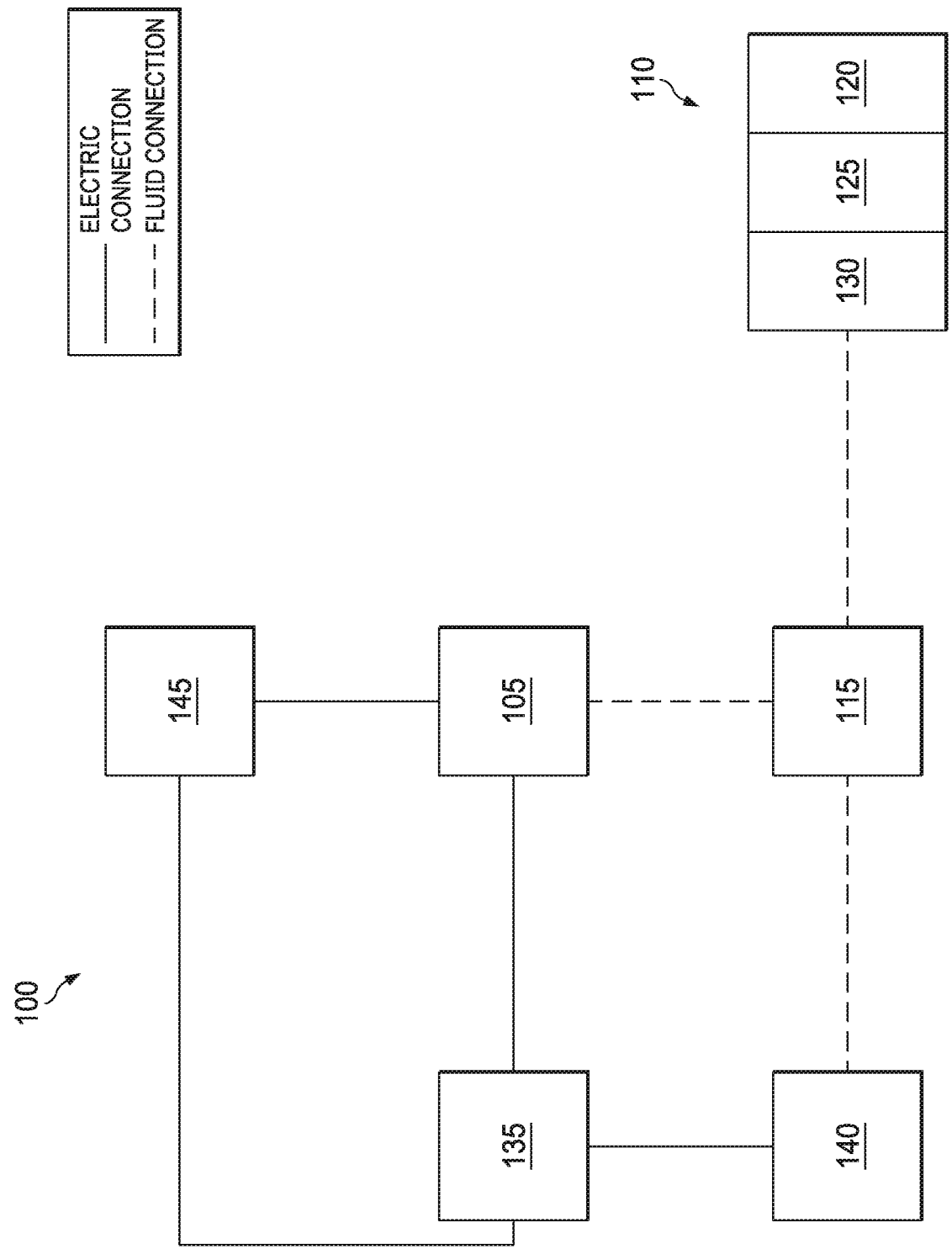
FIG. 1 is a simplified functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, surgical, acute, traumatic, subacute, and dehisced wounds; partial-thickness burns; ulcers (such as diabetic, pressure, or venous insufficiency ulcers); flaps; and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface 130 may facilitate coupling a fluid conductor to the dressing 110.

The therapy system 100 may also include a regulator or controller, such as a controller 135. Additionally, the therapy system 100 may include sensors to measure operating parameters and provide feedback signals to the controller 135 indicative of the operating parameters. As illustrated in FIG. 1, for example, the therapy system 100 may include a first sensor 140 and a second sensor 145 coupled to the controller 135.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 135 and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 135 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 135, may be a microprocessor or computer programmed to operate one or more components of the therapy system 100, such as the negative-pressure source 105. In some embodiments, for example, the controller 135 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 135 is also preferably configured to receive one or more input signals, such as a feedback signal, and programmed to modify one or more operating parameters based on the input signals.

Sensors, such as the first sensor 140 and the second sensor 145, are generally known in the art as any apparatus operable to detect or measure a physical phenomenon or property, and generally provide a signal indicative of the phenomenon or property that is detected or measured. For example, the first sensor 140 and the second sensor 145 may be configured to measure one or more operating parameters of the therapy system 100. In some embodiments, the first sensor 140 may be a transducer configured to measure pressure in a pneumatic pathway and convert the measurement to a signal indicative of the pressure measured. In some embodiments, for example, the first sensor 140 may be a piezo-resistive strain gauge. The second sensor 145 may optionally measure operating parameters of the negative-pressure source 105, such as a voltage or current, in some embodiments. Preferably, the signals from the first sensor 140 and the second sensor 145 are suitable as an input signal to the controller 135, but some signal conditioning may be appropriate in some embodiments. For example, the signal may need to be filtered or amplified before it can be processed by the controller 135. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface 120 may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas The thickness of the tissue interface 120 may also vary according to needs of a prescribed therapy. For example, the thickness of the tissue interface 120 may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; PU drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m²/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Figure 2:
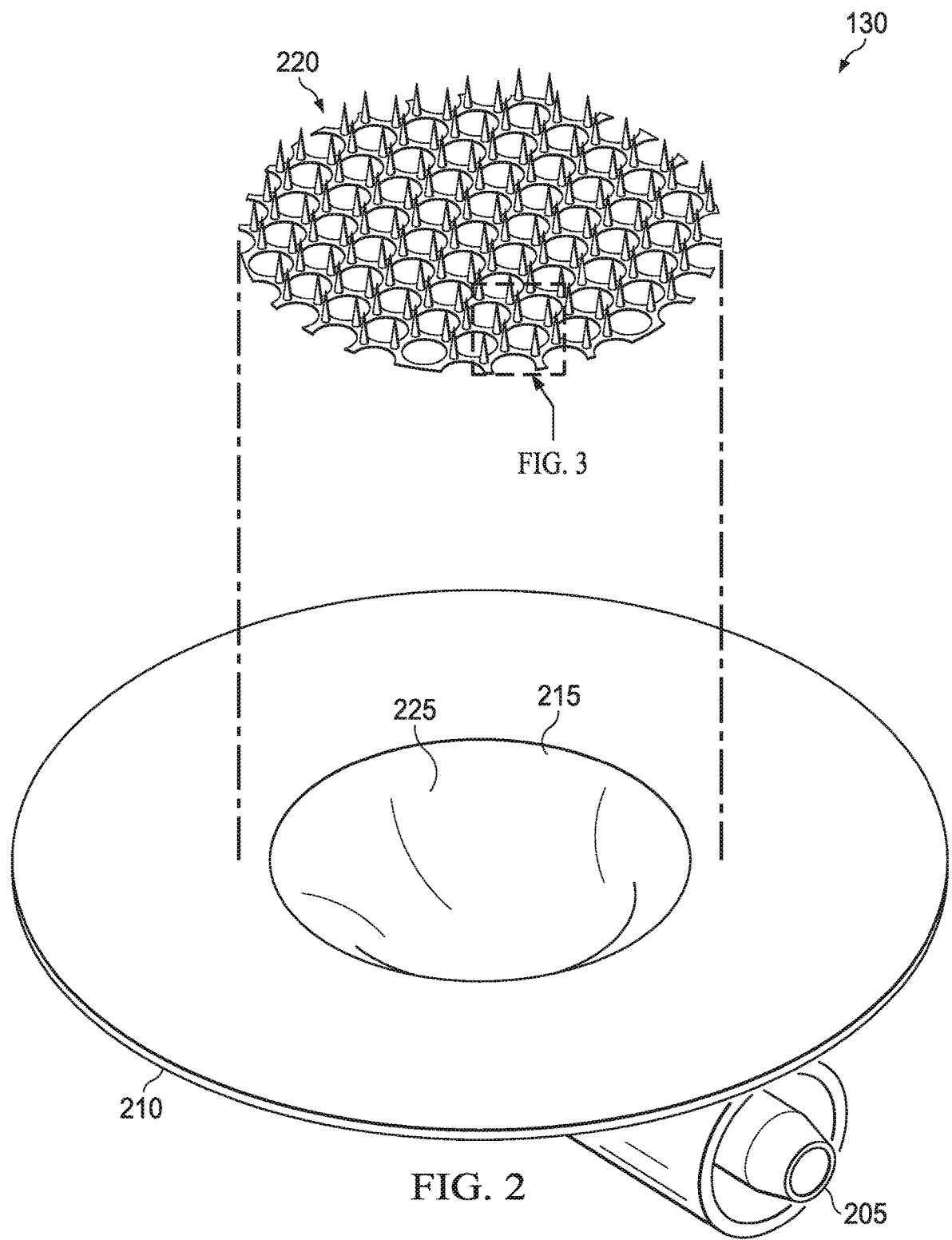
FIG. 2 is an assembly view of an example of a dressing interface that may be associated with some embodiments of the therapy system of FIG. 1.

FIG. 2 is an assembly view of an example of the dressing interface 130 of FIG. 1, illustrating additional details that may be associated with some embodiments. In the example of FIG. 2, the dressing interface 130 comprises a port 205, a base 210 having an aperture 215, and a microneedle array 220. A conduit 225 can fluidly couple the aperture 215 and the port 205. In some examples, an attachment device (not shown) such as a pressure-sensitive adhesive may be disposed on at least a portion of the base 210 adjacent to the aperture 215.

Figure 3:
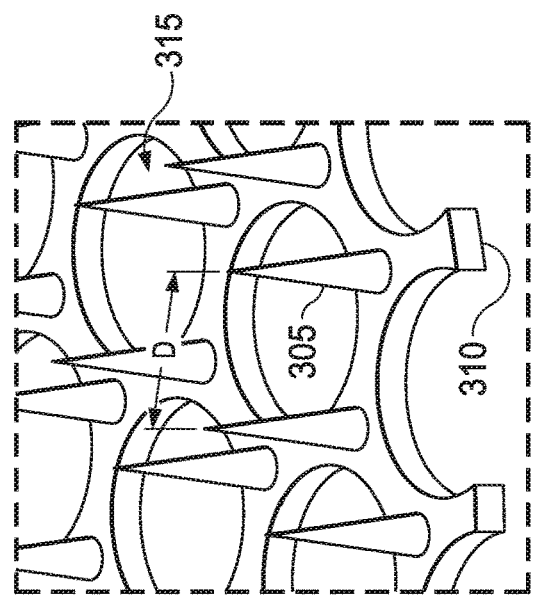
FIG. 3 is a detail view of a microneedle array that may be associated with the dressing interface of FIG. 2.

FIG. 3 is a detail view of the microneedle array 220 of FIG. 2, illustrating additional details that may be associated with some embodiments. For example, the microneedle array 220 may comprise a plurality of microneedles 305 and a substrate 310. Each of the microneedles 305 may be coupled at one end to the substrate 310. The substrate 310 may provide structural support for the plurality of microneedles 305. The substrate 310 may have sufficient flexibility to allow it to be placed on a contoured tissue site. For example, some embodiments of the substrate 310 may comprise a plurality of apertures 315, which can increase the flexibility of the substrate 310. The apertures 315 may have a variety of shapes, such as circles or hexagons. The microneedles 305 may be mutually separated by a distance D. The distance D may be measured by the distance from peak-to-peak of two microneedles 305. A distance D of about 1 millimeter may be suitable for some examples.

Figure 4:
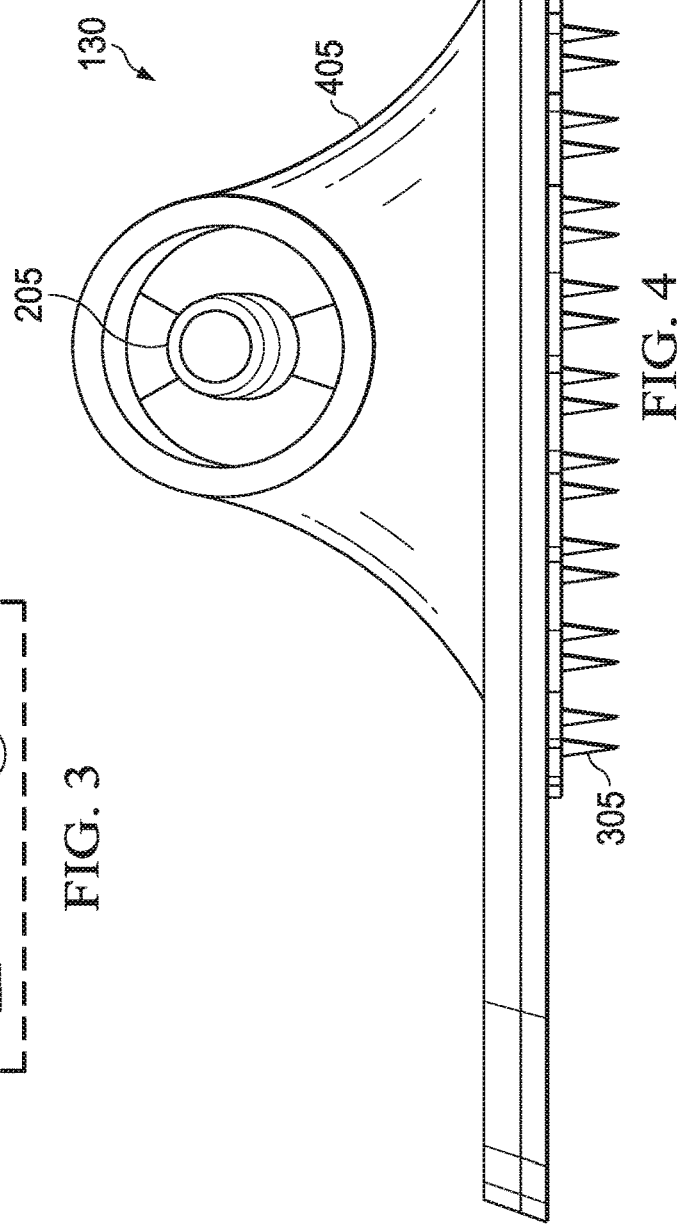
FIG. 4 is a front view of the dressing interface of FIG. 2, as assembled.

FIG. 4 is a front view of the dressing interface 130 of FIG. 2, as assembled, illustrating additional details that may be associated with some embodiments. As shown in the example of FIG. 4, the substrate 310 may be coupled to the base 210. The port 205 may be supported by a housing 405.

Figure 5:
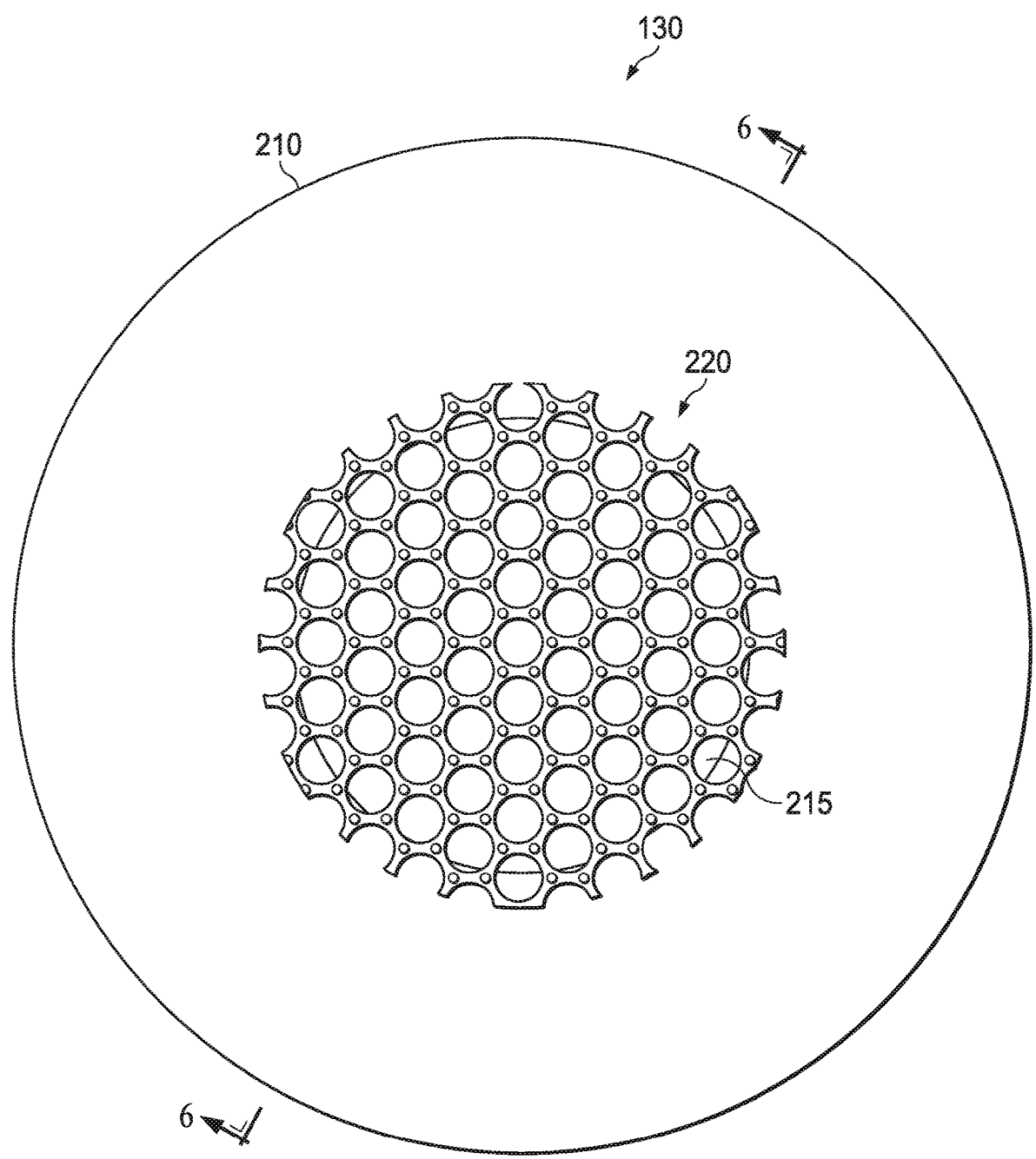
FIG. 5 is a plan view of the dressing interface of FIG. 4, illustrating the microneedle array disposed over the aperture in the base.

FIG. 5 is a plan view of the dressing interface 130 of FIG. 4, illustrating the microneedle array 220 disposed over the aperture 215 in the base 210.

Figure 6:
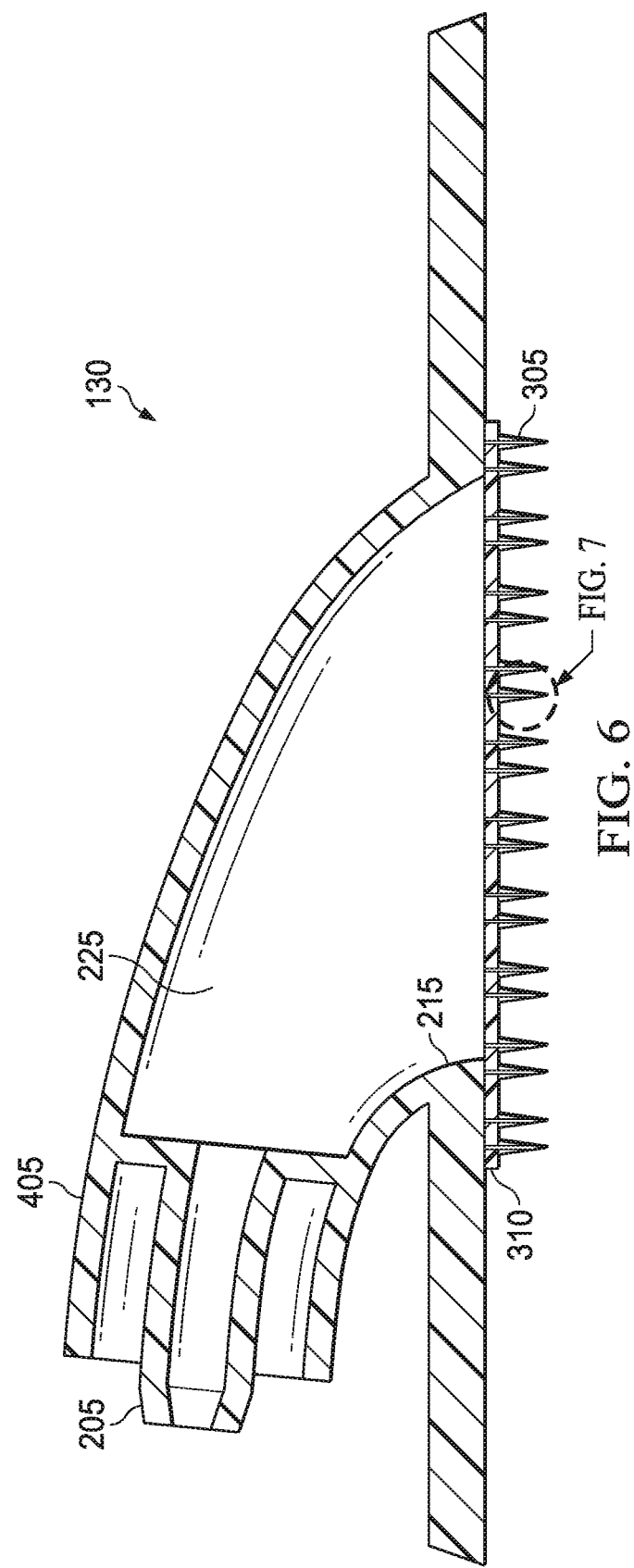
FIG. 6 is a section view of the dressing interface of FIG. 5 taken along line 6-6.

FIG. 6 is a section view of the dressing interface 130 of FIG. 5 taken along line 6-6, illustrating additional details that may be associated with some embodiments. In the example of FIG. 6, the housing 405 may provide or define the conduit 225 between the port 205 and the aperture 215. In some embodiments, the conduit 225 may comprise a bend between the aperture 215 and the port 205, which can reduce the height of the dressing interface 130. In some examples, a bend in a range of about 80 degrees to about 100 degrees may be suitable. A bend of about 90 degrees may be particularly advantageous in some embodiments. Each of the microneedles 305 may be fluidly coupled to the conduit 225 through the substrate 310.

Figure 7:
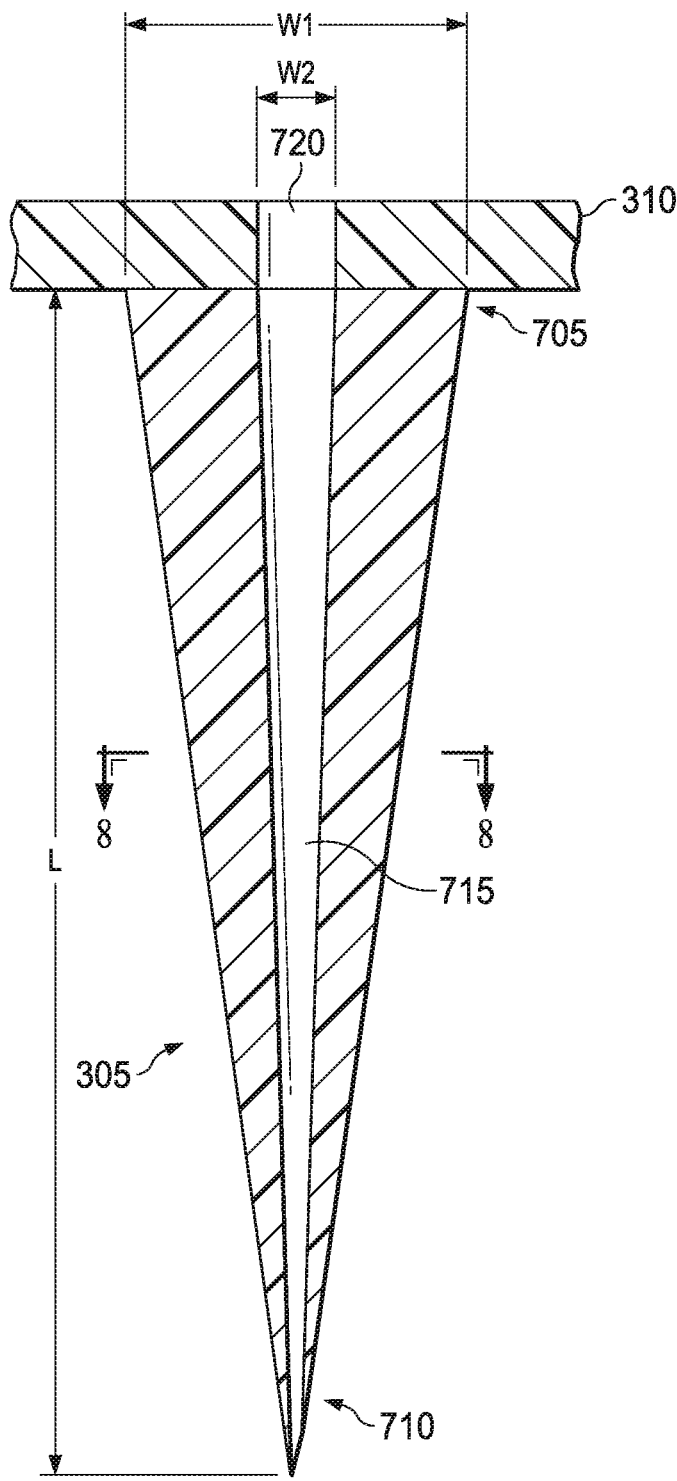
FIG. 7 is a partial detail view of the microneedle array of FIG. 6.

FIG. 7 is a partial detail view of the microneedle array 220 of FIG. 6, illustrating additional details that may be associated with some embodiments. For example, each of the microneedles 305 may have a length L. A length L in a range of about 100 micrometers to about 4000 micrometers may be suitable for some embodiments. In some preferred embodiments the length L may be in a range of about 1000 micrometers to about 2000 micrometers. Each of the microneedles 305 may have a width W1. A width W1 in a range of about 200 micrometers to about 2000 micrometers may be suitable for some embodiments.

The microneedles 305 of FIG. 7 each comprise a first end 705, a second end 710, and a passage 715 between the first end 705 and the second end 710. The passage 715 may be created by means of precise laser cutting or chemical etching. The passage 715 has a width W2. A width W2 of about 20 micrometers to about 1800 micrometers may be suitable for some examples. In some preferred embodiments the width W2 may be in a range of about 50 micrometers to about 1500 micrometers. In some embodiments, the microneedles 305, the passage 715, or both may be tapered. A taper in a range of about 0 degrees to about 45 degrees may be suitable for some embodiments. In some preferred embodiments, the taper may be in a range of about 2 degrees to about 20 degrees.

In FIG. 7, the width of the microneedles 305 decreases with distance from the substrate 310. The width of the passage 715 may also decrease with distance from the substrate 310. The width W1 and the width W2 of FIG. 7 are the maximum width of the microneedles 305 and the passage 715, respectively, which generally corresponds to the width W1 and the width W2 at the first end 705.

In a particular example, the microneedles 305 may have a passage width W2 in a range of about 1000 micrometers to about 1500 micrometers. This width W1 may result in an area for fluid flow in a range of about 0.8 square millimeters to about 1.76 square millimeters per microneedle 305.

The substrate 310 may also comprise a plurality of passages, channels, or other through-holes. For example, the substrate 310 may have an aperture 720 corresponding to each of the microneedles 305. As illustrated in FIG. 7, the aperture 720 may be fluidly coupled to the passage 715. In some embodiments, for example, the first end 705 of the microneedles may be coupled to the substrate 310 so that the passage 715 aligns with the aperture 720. The aperture 720 may have the same width as the passage 715 in some examples. The passage 715 is generally exposed through the second end 710.

Figure 8:
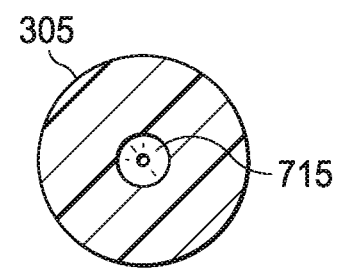
FIG. 8 is a sectional view of the microneedle of FIG. 7 taken along line 8-8.

FIG. 8 is a section view of the microneedle 305 of FIG. 7, taken along line 8-8. As illustrated in the example of FIG. 8, the microneedle 305 and the passage 715 may have circular and concentric cross-sections.

The microneedles 305 may be formed from a variety of biocompatible materials, such as stainless steel, titanium, aluminum, polycarbonate, polyethylene terephthalate, polyetherketone, polyimide, or polyphenylsulfone. The substrate 310 may be formed of a similar material as the microneedles 305. In some embodiments, the microneedles 305 may be coated with active agents that assist during the process of wound healing. The active agents may include anti-bacterial agents or biocompatible polymers such as collagen or hyaluronic acid.

Figure 9:
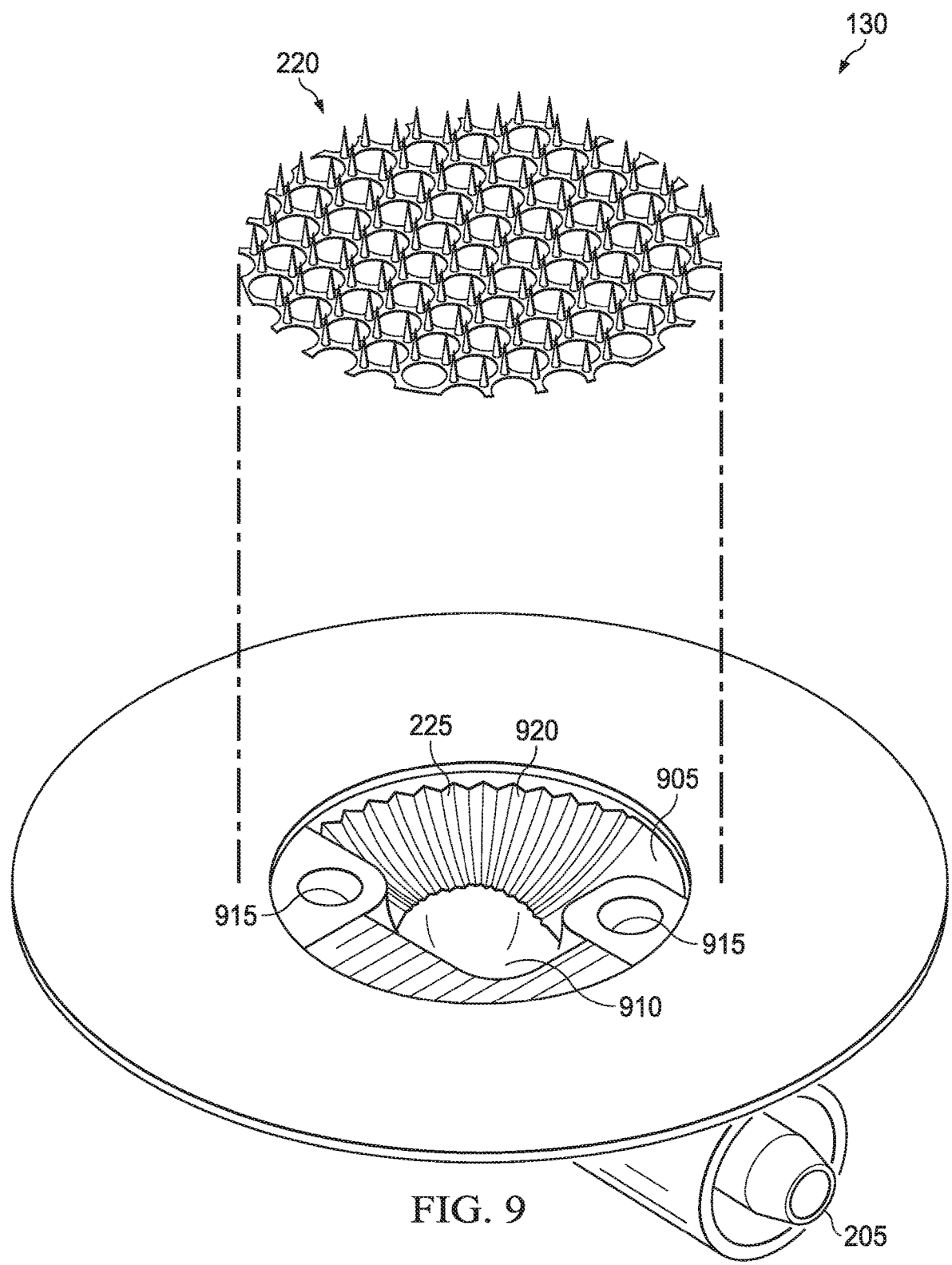
FIG. 9 is an assembly view of another example embodiment of a dressing interface.

FIG. 9 is an assembly view of another example of the dressing interface 130, illustrating additional details that may be associated with some embodiments. In the example of FIG. 9, the conduit 225 comprises an entry surface 905, a primary lumen 910, and one or more ancillary lumens 915. Optionally, the entry surface 905 comprises one or more channels 920, which can be configured to direct liquid from the entry surface 905 toward the primary lumen 910. The channels 920 may also be configured to direct liquid away from the ancillary lumens 915.

Figure 10:
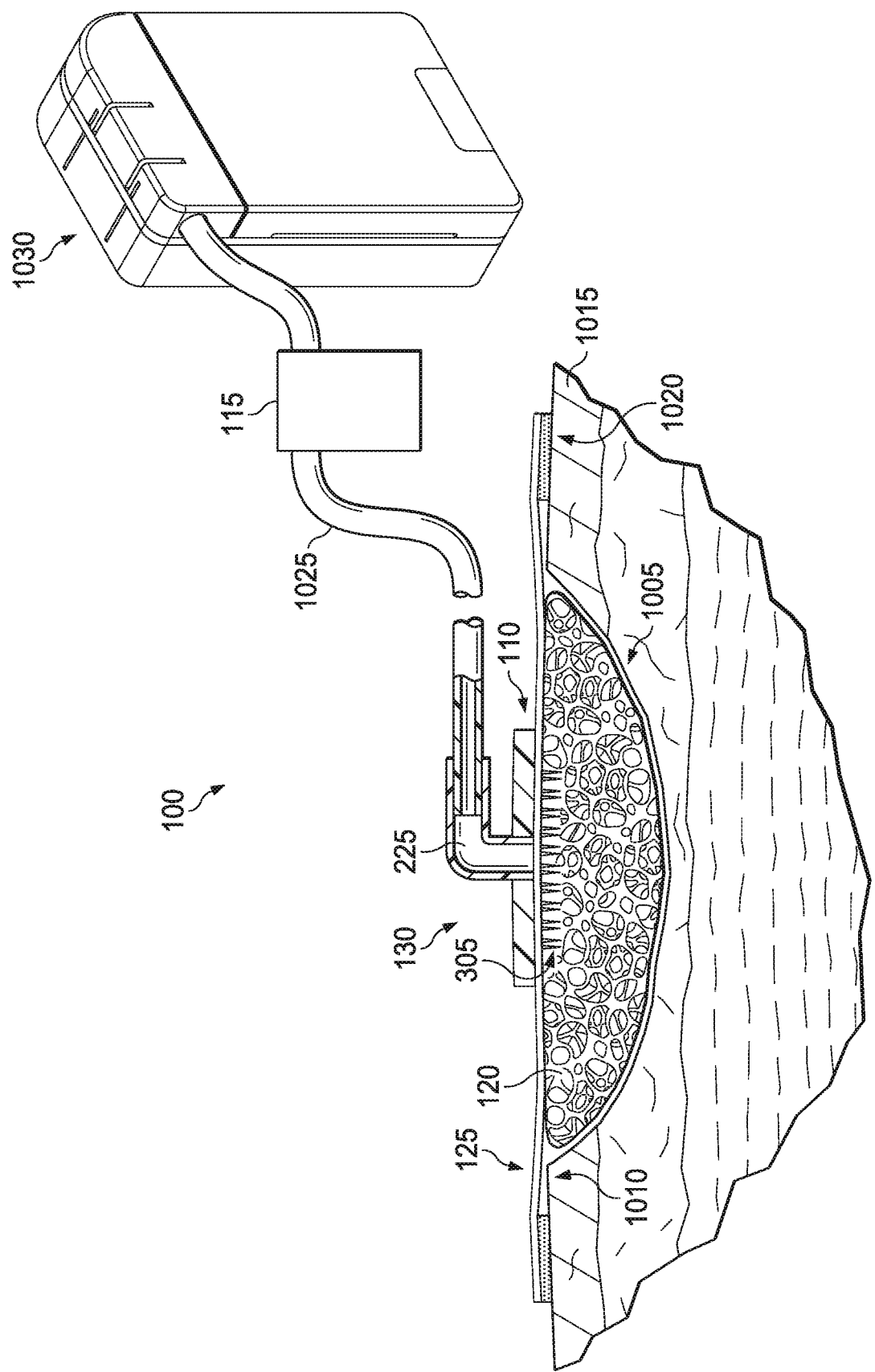
FIG. 10 is a schematic diagram of an example of the therapy system of FIG. 1 applied to a tissue site.

FIG. 10 is a schematic diagram of an example of the therapy system 100 applied to a tissue site 1005. In general, the tissue interface 120 may be applied to the tissue site 1005, and the cover 125 may be disposed over the tissue interface 120 around the tissue site 1005. The dressing interface 130 may be disposed on the cover 125, and pressure can be applied to the dressing interface 130 to pierce the cover 125 with the microneedles 305. In some examples, the pressure needed to penetrate the cover may be no greater than about 2N. The tapering of the microneedles 305 can substantially reduce or prevent blockage of the passage 715 (not shown in FIG. 10) by material that may be separated from the cover 125 when the microneedles 305 puncture the cover 125. A fluid conductor may be fluidly coupled to the dressing interface 130, and the negative-pressure source 105 (not shown) can be fluidly coupled to the fluid conductor. The negative-pressure source 105 can apply a therapeutic level of negative pressure to the tissue interface 120 through the fluid conductor and the dressing interface 130.

In the example of FIG. 10, the tissue site 1005 comprises a surface wound having an edge 1010 and epidermis 1015 adjacent to the edge 1010. The tissue interface 120 of FIG. 9 may comprise or consist essentially of a manifold. As illustrated, the tissue interface 120 can be placed within, over, on, or otherwise proximate to the tissue site 1005. The cover 125 may be placed over the tissue interface 120. The tissue interface 120 and the cover 125 may be assembled before application or in situ.

In some examples, the cover 125 may comprise an adhesive 1020. In some examples, the adhesive 1020 may be a medically-acceptable, pressure-sensitive adhesive that extends about a periphery, a portion, or an entire surface of each of the cover 125. In some embodiments, for example, the adhesive 1020 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 1020 may be continuous or discontinuous. Discontinuities in the adhesive 1020 may be provided by apertures or holes (not shown) in the adhesive 1020. The apertures or holes in the adhesive 1020 may be formed after application of the adhesive 1020 or by coating the adhesive 1020 in patterns on a carrier layer or the cover 125. Apertures or holes in the adhesive 1020 may also be sized to enhance the MVTR of the cover 125 in some example embodiments.

The cover 125 may be sealed to an attachment surface near the tissue site 1005. In FIG. 10, for example, the adhesive 1020 may seal the cover 125 to undamaged portions of the epidermis 1015. Thus, the dressing 110 can provide a sealed therapeutic environment adjacent to the tissue site 1005, substantially isolated from the external environment.

FIG. 10 also illustrates one example of a fluid conductor 1025 and the dressing interface 130. As shown in the example of FIG. 10, the fluid conductor 1025 may be a flexible tube, which can be fluidly coupled on one end to the dressing interface 130. In some examples, the tissue interface 120 can be applied to the tissue site 1005 before the cover 125 is applied over the tissue interface 120. The dressing interface 130 can be placed over the cover 125, and the microneedles 305 can pierce the cover 125 as illustrated in FIG. 10. The microneedles 305 may also penetrate a portion of the tissue interface 120, without contacting the tissue site 1005.

The passages 715 (not shown in FIG. 10) in the microneedles 305 can provide a fluid path between the tissue interface 120 and the conduit 225, which can be fluidly coupled to the fluid conductor 1025. The configuration of the microneedles 305, including the number, spacing, and size of the microneedles, can be varied for particular applications. For example, a configuration for achieving suitable levels of therapeutic negative pressure may comprise an array of 72 of the microneedles 305, each having a passage diameter of about 1000 micrometers to about 1500 micrometers. The peak-to-peak separation of the microneedles 305 may be about 1 millimeter. Such a configuration may result in a total effective area for fluid flow of at least 125 square millimeters and may be particularly advantageous for therapy pressures in a range of about −50 mmHg to about −200 mmHg.

An adhesive or other attachment device may couple the dressing interface 130 to the cover 125. In some examples, the adhesive used to couple the dressing interface 130 to the cover 125 may be a pressure sensitive adhesive.

The therapy system 100 of FIG. 10 comprises a therapy unit 1030, which can incorporate the negative-pressure source 105 (not shown) and the controller 135 (not shown). In operation, the negative-pressure source 105 can reduce pressure in the sealed therapeutic environment between the cover 125 and the tissue site 1005. The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively as "delivering," "distributing," or "generating" negative pressure, for example.

Negative pressure applied across the tissue site 1005 through the tissue interface 120 in the sealed therapeutic environment can induce macro-strain and micro-strain in the tissue site 1005. Negative pressure can also remove exudate and other fluid from a tissue site 1005, which can be collected in container 115.

The arrangement of the microneedles 305 can provide redundant flow paths through the dressing interface 130, which may substantially reduce or prevent blockages.

Additionally, the length of each of the microneedles 305, relative to the thickness of the tissue interface 120, may be sufficiently small to substantially reduce or prevent contact with the tissue site 1005. For example, in some embodiments, the tissue interface 120 may have a thickness of about 3 centimeters at atmospheric pressure, and the microneedles 305 may have a length L of about 1 millimeter. At therapeutic levels of negative pressure, the tissue interface 120 may compress to a thickness of about 3 millimeters, which can also separate the tissue site 1005 from the microneedles 305.

In some embodiments, the controller 135 may receive and process data from one or more sensors, such as the first sensor 140 (FIG. 1). The controller 135 may also control the operation of one or more components of the therapy system 100 to manage the pressure delivered to the tissue interface 120. In some embodiments, the controller 135 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 135. The target pressure may vary from tissue site to tissue site based on the type of tissue forming a tissue site, the type of injury or wound (if any), the medical condition of the patient, and the preference of the attending physician. After selecting a desired target pressure, the controller 135 can operate the negative-pressure source 105 in one or more control modes based on the target pressure and may receive feedback from one or more sensors to maintain the target pressure at the tissue interface 120.

In some embodiments, the controller 135 may have a continuous pressure mode, in which the negative-pressure source 105 is operated to provide a constant target negative pressure for the duration of treatment or until manually deactivated. Additionally or alternatively, the controller 135 may have an intermittent pressure mode. For example, the controller 135 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 135 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 135, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

The systems, apparatuses, and methods described herein may provide significant advantages. For example, the microneedle structure can allow attachment of the interface to the drape without additional preparation or tools, which can significantly improve application time and reduce the risk of leaks.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 135 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An interface for fluidly coupling a fluid conductor to a tissue site through a cover, the interface comprising:
   a port configured to receive the fluid conductor;
   a base including an aperture disposed through the base;
   a conduit between the port and the aperture through the base;
   a microneedle substrate including a plurality of apertures and a plurality of passages disposed through the microneedle substrate: and
   a plurality of microneedles coupled to the substrate and disposed over the aperture through the base, each of the microneedles comprising a passage corresponding to one of the plurality of passages disposed through the microneedle substrate and fluidly coupled to the aperture through the base
   wherein the plurality of apertures are distinct from and adjacent to the plurality of passages.

2. The interface of claim 1, wherein each of the microneedles has a length in a range of 100 micrometers to 4000 micrometers, and a maximum width in a range of 200 micrometers to 2000 micrometers.

3. The interface of claim 1, wherein the passage of each of the microneedles has a maximum width in a range of 20 micrometers to 1800 micrometers.

4. The interface of claim 1, wherein each of the microneedles is tapered.

5. The interface of claim 1, wherein the passage of each of the microneedles is tapered in a range of 0 degrees to 45 degrees.

6. The interface of claim 1, wherein the plurality of microneedles are arranged in an array over the aperture.

7. The interface of claim 1, wherein the microneedle substrate is coupled to the base, and wherein the plurality of apertures through the microneedle substrate are configured to increase a flexibility of the microneedle substrate.

8. The interface of claim 1, wherein each of the microneedles is formed from a biocompatible material.

9. The interface of claim 1, wherein each of the microneedles is formed from stainless steel, titanium, aluminum, polycarbonate, polyethylene terephthalate, polyetherketone, polyimide, or polyphenylsulfone.

10. The interface of claim 1, wherein the plurality of microneedles are mutually separated by a distance of 1 millimeter.

11. The interface of claim 1, wherein the plurality of microneedles provide an effective area for fluid flow of at least 125 square millimeters.

12. The interface of claim 1, wherein the plurality of microneedles are configured to pierce the cover.

13. The interface of claim 1, wherein:
    the conduit comprises an entry surface and channels on the entry surface; and
    the channels are adapted to direct liquid into the port.

14. The interface of claim 1, wherein:
    the conduit comprises an entry surface, a primary lumen, and an ancillary lumen;
    the entry surface comprises one or more channels; and
    the channels are adapted to direct liquid into the primary lumen.

15. The interface of claim 1, wherein:
    the conduit comprises a primary lumen and an ancillary lumen;
    the conduit comprises an entry surface and channels on the entry surface; and
    the channels are adapted to direct liquid away from the ancillary lumen.

16. The interface of claim 1, wherein:
    the conduit comprises a primary lumen and an ancillary lumen;
    the conduit comprises an entry surface and channels on the entry surface; and
    the channels are adapted to direct liquid into the primary lumen and away from the ancillary lumen.

17. The interface of claim 1, wherein the conduit comprises a bend between the aperture through the base and the port.

18. A system for treating a tissue site with negative pressure, the system comprising:
    a manifold configured to be applied to the tissue site;
    a cover configured to be disposed over the manifold; and
    the interface of claim 1.

19. The system of claim 18, further comprising a negative-pressure source configured to be fluidly coupled to the interface.

20. A method for treating a tissue site with negative pressure, the method comprising:
    applying a manifold to a tissue site;
    sealing a cover over the manifold around the tissue site;
    disposing the interface of claim 1 on the cover;
    applying pressure to the interface to pierce the cover with the plurality of microneedles;
    fluidly coupling a fluid conductor to the port;
    fluidly coupling a negative-pressure source to the fluid conductor; and
    applying a therapeutic level of negative pressure from the negative-pressure source to the manifold through the fluid conductor and the interface.

* * * * *